United States Patent [19]
Gilbert

[11] Patent Number: 5,085,527
[45] Date of Patent: Feb. 4, 1992

[54] COMPUTER CONTROLLED MICROWAVE OVEN WATER CONTENT DETERMINATION

[75] Inventor: Paul A. Gilbert, Vicksburg, Miss.

[73] Assignee: The United States of America as represented by the Secretary of the Army, Washington, D.C.

[21] Appl. No.: 259,661

[22] Filed: Oct. 19, 1988

[51] Int. Cl.[5] ...................... G01N 25/02; G01G 23/00
[52] U.S. Cl. .......................................... 374/14; 73/76; 177/245
[58] Field of Search .............. 73/76; 177/245; 374/14; 219/10.55 B

[56] References Cited

U.S. PATENT DOCUMENTS

| Re. 32,861 | 2/1989 | Collins et al. ...................... 73/76 X |
|---|---|---|
| 3,890,825 | 6/1975 | Davis .................................. 73/76 X |
| 4,165,633 | 8/1979 | Raisanen ......................... 177/245 X |
| 4,168,623 | 9/1979 | Thomas, Jr. ............................ 73/76 |
| 4,316,384 | 2/1982 | Pommer et al. ................. 364/567 X |
| 4,406,070 | 9/1983 | Preston . |
| 4,466,198 | 8/1984 | Doll . |
| 4,481,409 | 11/1984 | Smith ....................... 219/10.55 B X |
| 4,483,082 | 11/1984 | Ellingson . |
| 4,606,650 | 8/1986 | Harris ............................. 177/245 X |

FOREIGN PATENT DOCUMENTS 1068515 12/1979 Canada .
983416 12/1982 U.S.S.R. .

OTHER PUBLICATIONS

Diprose et al., "The Measurement of Soil and Leaf Moisture Content by 2450 MHz Radiation", 14th Microwave Power Symposium 1979, Monaco, Jun. 11-15, 1979, pp. 137-140.

Primary Examiner—Daniel M. Yasich
Attorney, Agent, or Firm—Darrell E. Hollis

[57] ABSTRACT

Method and apparatus for water content determination of soil-water mixtures and of other materials through the use of microwave energy to rapidly dry the material being tested, drying and water content determination being controlled in a preferred embodiment by a computer interfaced with a microprocessor of a digital microwave oven. The invention preferably includes a digital microwave oven mechanically interfaced with a precision digital balance, the oven and balance being operatively interfaced with the computer. As drying in the microwave oven progresses, the computer monitors weigth loss of the test sample as indicated by the balance and controls microwave power levels according to program instructions. The invention is thereby capable of providing rapid, precise and repeatable water content determinations of suitable samples.

20 Claims, 2 Drawing Sheets

COMPUTER CONTROLLED MICROWAVE OVEN WATER CONTENT DETERMINATION

STATEMENT OF GOVERNMENT INTEREST

The invention described and claimed herein may be manufactured and used by or for the Government of the United States of America for governmental purposes without the payment of royalties thereon or therefor.

BACKGROUND OF THE INVENTION

1. Field of the Invention

The invention relates generally to method and apparatus for water content determination and particularly to computer-controlled microwave drying of material samples with precision and rapidity.

2. Description of the Prior Art

Moisture content determinations have conventionally been made through the use of ovens utilizing electrical resistance or gas heating. Use of conventional ovens for moisture determination require drying of a specimen of material over a specified period of time with a mass determination taken both before and after the drying period. Water content is usually taken to be the ratio of the mass of water to the mass of dry sample expressed as a percentage. Determination of water content according to the prior art thus described is certainly simple and accurate but it is also extremely slow. In construction situations where large quantities of soil are being placed and compacted, such as in the construction of embankment dams or large foundations, water content determinations of soils must be regularly taken since water content and density of soils dictate the strength characteristics and behavior of the soil. A soil structure compacted to an incorrect water content will experience performance and maintenance problems. However, in most construction situations it is not possible to wait up to 24 hours for a correct water content determination in a conventional oven. Accordingly, method and apparatus are required in such situations in order that a rapid and accurate water content determination can be performed. Other industrial situations wherein the availability of a rapid and accurate water content determination would be of benefit include the manufacture of paper pulp and wood pulp among others and also including the testing of seed, chemicals, fiber, etc. Although methodology exists for water content determination in a more rapid manner than is possible with conventional ovens, this prior methodology is not sufficiently accurate for the requirements of earthwork compaction control as well as in many other water content testing situations.

As examples of prior art which relates to testing for water content of a specimen, attention is directed to Preston U.S. Pat. No. 4,406,070 who discloses a method and apparatus for treating variable batches of moist material by the application of radio frequency energy in order to reduce the moisture content of the material. Radio frequency power brought to bear on the material is incrementally reduced by an electromechanical adjusting device.

Doll U.S. Pat. No. 4,466,198 describes the removal of moisture from wood by subjecting the wood to dielectric heating.

Ellingson, in U.S. Pat. No. 4,483,082, discloses the drying of fabric through microprocessor control. Russian patent 983,416 discloses a process of drying material by using electromagnetic oscillations. An initial moisture content and weight are fed to the memory of a microprocessor in the system described in the Russian patent, the microprocessor through an actuator switching on an electromagnetic oscillation to initiate the drying process. Canadian patent 1,068,515 describes method and apparatus for determining the weight and moisture content of materials disposed within a shipping container. A publication by Diprose et al resulting from the Fourteenth Microwave Power Symposium, June 11-15, 1979, in Monaco, is entitled "The Measurement of Soil and Leaf Moisture Content by 2450 MHz Radiation" and is located on pages 137-140 of the proceedings of that Symposium The Diprose et al publication discloses a process of using microwave radiation for soil drying. A soil sample is weighed, dried and then reweighed according to Diprose et al in order to determine the moisture content of the soil.

Although the Diprose et al article teaches the use of microwave radiation for drying a material and the Russian patent discloses a microprocessor control for a material drying process, the prior art noted above does not disclose a drying apparatus utilizing a computer to monitor weight loss during microwave drying operations and further to adjust microwave power according to conditions existing as drying progresses.

Accordingly, the prior art has not met the long felt need in the art for a rapid, precise and reproducible method for determining water content in a specimen and especially to an accuracy which would be equivalent to that accomplished in a conventional, constant oven maintained at 110° C., for example, and which is sufficiently rapid so as to be utilizable on site for proper earthwork compaction control during a construction process.

SUMMARY OF THE INVENTION

The invention provides both method and apparatus for water content determination of soil-water mixtures and of other materials for which water content determinations are necessary in use and/or processing. In basic embodiments of the invention, microwave energy is utilized to rapidly dry a sample so that rapid water content determination can be accomplished. The apparatus of the invention is configured and programmed so that a soil-water mixture or other sample can be dried in a controlled manner, the apparatus being automated and programmed to dry the sample such that the entire process is independent of operator influence and is precisely repeatable. According to the invention, microwave drying of a sample is controlled so as to be precise and repeatable by monitoring weight loss of the test sample as drying progresses. A computer monitors sample weight loss and changes microwave power response and power application to the sample in accordance with conditions existing as drying progresses. The apparatus comprises a computer and a precision digital balance in a preferred embodiment such that the microwave oven can be precisely controlled.

In a preferred embodiment, a digital microwave oven is interfaced with a computer through a microprocessor which is a part of the oven. The microwave oven is mounted with a precision digital balance on a rigid frame with the probe of the balance extending into the oven. A weighing platform is mounted on the probe of the digital balance and receives the sample for which water content determination is to be accomplished. The computer communicates with the digital balance and with the microprocessor of the microwave oven such that the computer is enabled to activate the balance, zero the balance, acquire and process data directly from the balance and to make decisions on the manner in which the drying process is to proceed while manipulating the microwave oven by communicating directly with the microprocessor or microprocessors of the oven.

The present methodology and apparatus enable a timewise increase by a factor of from 10 to 100 over conventional oven methods, the present apparatus being more reliable, repeatable and systematic than prior apparatus for water content determination. Computer control of the drying process greatly reduces the probability of introducing errors due to human bias in operating technique when a microwave oven is used to manually dry soils with human judgment being relied upon for process control. Manual control of microwave drying of test samples usually results in over drying or under drying with results being imprecise at best.

Accordingly, it is an object of the invention to provide method and apparatus for water content determination of samples such as soil-water mixtures through the use of microwave drying albeit with precise control of the microwave drying operation by computer monitoring of weight loss during the drying operation coupled with adjustment of microwave power as drying progresses.

It is another object of the invention to provide method and apparatus for water content determination of suitable samples wherein apparatus used to practice the methods of the invention include a microwave oven communicating with a computer through at least one microprocessor, the computer also being digitally coupled to a precision digital balance such that the computer controls operation of the balance and the microwave oven according to a program exactly dependent upon information received by the computer from the digital balance.

A further object of the invention is to provide method and apparatus for monitoring weight loss of a sample for which moisture content determination is to be accomplished, the weight loss of the sample being continuously monitored as drying by microwave progresses, the power response of the microwave source being altered with concomitant power application to the test sample being varied according to a predetermined program responsive to the weight loss profile of the sample.

Further objects and advantages of the invention will become more readily apparent in light of the following detailed description of the preferred embodiments.

DESCRIPTION OF THE PREFERRED EMBODIMENTS

Figure 1:
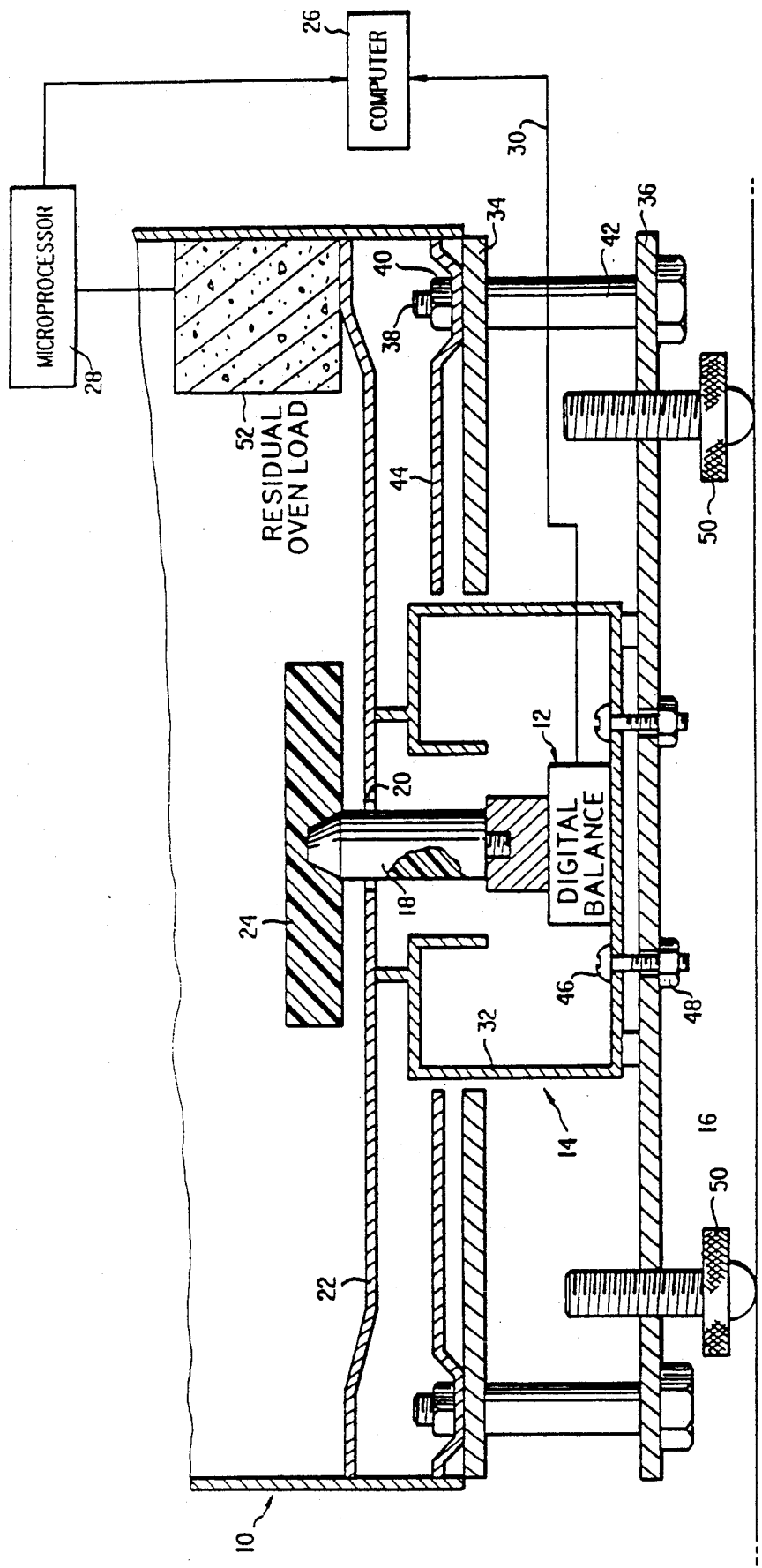
FIG. 1 is a schematic of a mechanically combined microwave oven and precision digital balance, the oven and balance being operatively connected to a computer; and, FIG. 2 is a flow chart of a preferred microwave drying process according to the invention.

Referring now to FIG. 1, a microwave oven is seen at 10 with the upper portion of the oven being removed for ease of illustration. A precision digital balance 12 is seen to be mounted underneath the oven 10 on a rigid frame 14. The frame 14 is further mounted to exterior frame 16 on which the microwave oven 10 is also mounted as will be further described hereinafter. The digital balance 12 inherently includes a probe 18 which extends into the microwave oven 10 through an opening 20 formed in lower wall 22 of the oven 10. The opening 20 communicates with the interior of the frame 14 which is sealed from ambient to avoid leakage of microwave energy. The probe 18 is thus not contacted by edge portions of the lower wall 22 defining the opening 20. A weighing platform 24 is disposed at the distal end of the probe 18, the platform being formed of a material such as polyethylene, Teflon, or other material which is unreactive to microwave energy. A sample (not shown) which is to be tested is disposed on the weighing platform 24 and the oven 10 is then closed so that initialization procedures can be accomplished according to a program operated computer 26.

The computer 26 is shown schematically to be operatively connected to microprocessor 28. Microwave ovens such as the microwave oven 10 are conventionally provided with microprocessor controls and interfacing between a microprocessor control such as the microprocessor 28 and a computer such as the computer 26 is conventional in the art. The microprocessor 28 conveniently comprises a digital processor. The computer 26 also interfaces with the digital balance 12, a convenient connection being via a RS 232 interface cable 30 such as is conventional in the art. The computer can be conveniently chosen to comprise a small computer such as a 64 K RAM computer as is conventional in the art. The computer 26 is thus interfaced with the microprocessor 28 of the microwave oven 10 and also with the digital balance 12 as aforesaid.

The frame 14 mounting the digital balance 12 includes an enclosing balance case 32 which houses the digital balance 12 and mates with the lower wall 22 of the oven 10 to provide a sealed housing for the probe 18 of the balance 12 to extend into the interior of the microwave oven 10. Both the balance 12 and the microwave oven 10 are fastened rigidly together on the exterior frame 16, the frame 16 comprising upper and lower plates 34 and 36 which are rigidly held together by means of appropriate bolts 38, nuts 40 and spacer sleeves 42. The bolts 38 and nuts 40 conveniently attach to the plates 34 and 36 and to an exterior wall 44 of the oven 10. The frame 14 housing the digital balance 12 and supporting said balance is preferably attached to the plate 36 by means of screws 46 and nuts 48 as seen in FIG. 1. The plate 36 is further provided with leveling screws 50 such as are conventionally employed for leveling of a balance such as the digital balance 12. Typically, three of the leveling screws 50 are utilized in a conventional manner even though only two of the screws 50 are shown in FIG. 1.

In essence, the computer 26 under the control of appropriate software acquires and processes data directly from the balance 12 and, based on the acquired data, makes decisions as to the conduct of the drying process. Based on these decisions, the operation of the microwave oven 10 is manipulated by direct communication with the microprocessor 28. As is conventional in the art, the microprocessor 28 controls power to the microwave oven 10 and connects in a conventional manner with a residual oven load 52.

Figure 2:
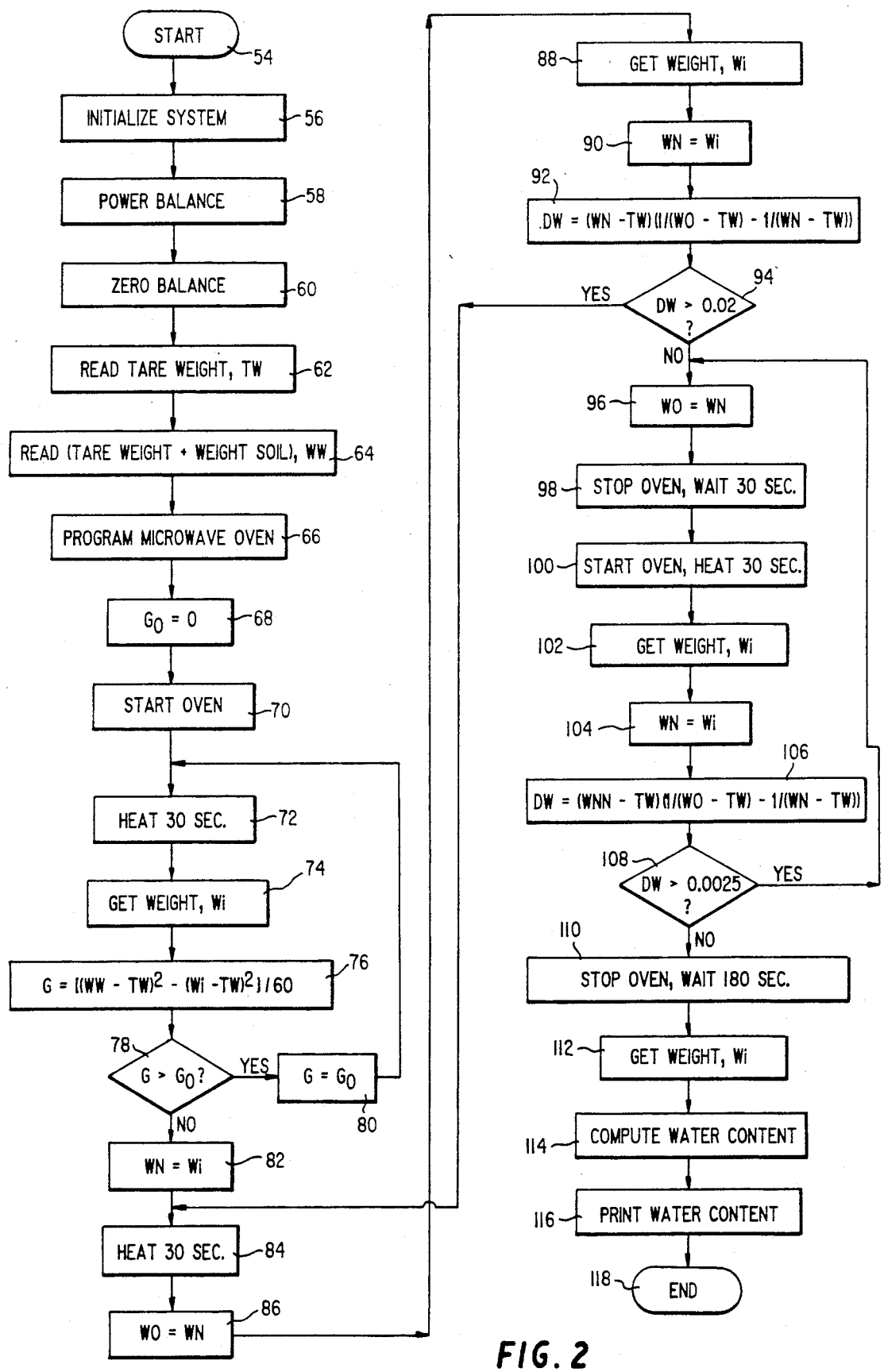

The computer 26 initiates operation of the apparatus by activating the balance 12 and zeroing the balance. A sample (not shown) of a material which is to be analyzed is placed on the weighing platform 24 and the microwave oven 10 is activated such that microwave energy is directed on the sample. The digital balance 12 provides data to the computer 26 as to the weight of the sample as drying progresses. Based upon the data received from the balance 12 by the computer 26, weight loss from the sample is monitored during the microwave drying operation and the power to the microwave oven 10 is adjusted as drying progresses. The flow chart of the drying process is shown in FIG. 2 which illustrates the complete logic for three different levels of microwave drying. Microwave drying is terminated by the computer 26 when a limiting per cent weight change occurs with time, this value being expressed as a slope. The slope figure used in software such as controls the computer 26 is determined by calibrating the microwave oven 10 against a conventional oven over a broad database including soil samples of differing types. Therefore, the data employed for construction of the slope figure used to produce the software driving the computer 26 is empirically determined. Computer control of the drying process greatly reduces the probability of introducing errors due to human bias and operating technique when a microwave oven is used to manually dry soils, human judgment conventionally being employed for process control in such situations.

Referring now to FIG. 2, the program logic employed in operation of the present apparatus is shown in flow chart form as beginning with a start step 54 which includes system initialization at step 56 involving initiating power to the balance 12 at step 58. At step 60, the balance 12 is zeroed and the tare weight is read at 62. The weight of the soil sample is read at step 64.

The microwave oven 10 is programmed at step 66 with initialization occurring at step 68 and oven start occurring at step 70. Under conditions where $G_0 = 0$, the computer 26 commands the microwave oven 10 to heat for 30 seconds at step 72 whereupon the computer determines weight Wi at step 74 and then computes a G value at step 76, the G value being dependent upon the difference value between tare weight plus soil weight minus tare weight squared minus weight $W_i$ minus tare weight squared divided by 60. In the event that G is greater than $G_0$ as determined at step 78, the program leads either to step 80 where G is equal to $G_0$ or to step 82 where $WN = W_i$ at 82. If G equals $G_0$, the system cycles back in a closed loop to oven start. If G is greater than $G_0$ and the system cycles to step 82, then the oven is commanded to heat for 30 seconds at step 84 and proceeds through step 86 wherein WO = WN. WN is an arbitrarily created term commonly found in computer programs having loops therein. The term is used to store the proper current value of a variable which will later be used in an equation. For example, the value of WN is set to the value of Wi at block 82. Then the value of WO is set to the value of WN at block 86 after heating the soil sample (block 84). Then the sample is weighed to obtain its new weight Wi. Then WN is once again set to Wi. Note that the value of Wi has changed due to the heating of the soil sample. At this point DW is calculated using the current values stored in WN, TW and WO. When the loop is repeated the values of WN and WO will change and these new values of WN and WO will be used to calculate DW. DW represents the rate of decrease in water content of the soil sample during the 30 second heating interval (block 84). The cycle continues through step 88 wherein the weight $W_i$ is obtained, WN being equal to $W_i$ as shown at step 90 with processing at step 92 to determine a value DW as shown in the flow chart. In the event that DW is greater than 0.02, an empirical figure, then the computer cycles the process back to step 82. In the event that DW is not greater than 0.02, then the program proceeds through steps 94 and 96 wherein WO is equal to WN and the operation of the oven 10 is stopped at step 98 for 30 seconds. At step 100, the oven is started and heated for 30 seconds with the weight $W_i$ being obtained at step 102 wherein the identity of WN and $W_i$ is shown at step 104. The value of DW is then computed with the value of DW then being compared to 0.0025, an empirical figure, to determine whether DW is greater than 0.0025. In the event that DW is greater, the system cycles back to step 94 from steps 106 and 108. In the event that DW is not greater than 0.0025, then the system cycles from step 108 to step 110 whereupon the oven is stopped and a delay of 180 seconds is indicated. The weight $W_i$ is then obtained at step 112 and water content is computed at step 114. Water content is then printed out at step 116 whereupon the program ends at 118.

During stage three, applying full power to the sample for a 30 second interval and then terminating power for a 30 second interval as shown by blocks 98 and 100 results in microwave energy being applied intermittently to the sample as the loop defined by blocks 96–108 is repeatedly traversed.

The invention is thus seen to comprise method and apparatus wherein water content determinations of samples can be obtained through computer control of a microwave oven. In its most broad sense, the invention monitors weight loss of a test sample as drying progresses, the power application to the test sample being changed in response to monitored weight loss to produce precisely controlled and programmed drying of the test sample. The method and apparatus of the invention can be practiced and configured other than as expressly shown and described herein, the scope of the invention being set forth in the appended claims.

What is claimed is:

1. A method for determining the volatile material content of a sample, comprising the steps of:
   a. disposing the sample on a weighing platform located within an enclosure;
   b. determining the initial weight of the sample;
   c. applying microwave energy to the sample during a variable drying period, said variable drying period including a plurality of portions;
   d. monitoring the rate of weight loss of the sample during the drying period; and
   e. controlling the application of microwave energy to the sample during the variable drying period in response to the monitored weight loss rate to determine the length of the variable drying period with said microwave energy being applied intermittently during a portion of the variable drying period thereby precisely controlling the drying of the sample;
   f. determining the final weight of the sample at the end of the variable drying period; and
   g. determining the loss of volatile material by using the final weight and the initial weight.

2. The method of claim 1 wherein the volatile material comprises water.

3. The method of claim 1 wherein the initial weight of a sample is determined by the balance on programmed instructions from a computer, the computer storing the initial weight information.

4. The method of claim 1 wherein a computer controls the application of microwave energy to the sample.

5. The method of claim 1 wherein the step of controlling includes the following steps:
   a. applying uninterrupted microwave energy to the sample during a first portion of the variable drying period; and
   b. applying microwave energy intermittentally to the sample during a second portion of the variable driving period.

6. The method of claim 5 wherein said first portion includes
   a. an initial portion during which the sample's temperature increases from the ambient temperature to a temperature where the volatile material begins to be driven from the sample at a substantially higher rate than during the initial portion, the volatile material being driven from the sample at a substantially slow rate during the initial period; and
   b. a middle portion during which the volatile material is driven from the sample at a rate substantially higher than the substantially slow rate provided during the initial portion.

7. The method of claim 6 wherein the second portion follows the middle portion and during the second portion the volatile material is driven from the sample at a substantially lower rate than during the middle portion.

8. The method of claim 1 wherein the weighing platform is fabricated from a material that is unreactive to microwave energy.

9. The method of claim 1 wherein the step of controlling includes the following steps:
   a. applying uninterrupted microwave energy to the sample until a first limit value is detected, the first limit value indicating that most of the volatile material has been driven from the sample; and
   b. applying microwave energy intermittentally to the sample until a second limit value is detected, the second limit value indicating that further application of microwave energy to the sample could result in damage of the sample.

10. The method of claim 9 wherein the uninterrupted microwave energy applying step includes detecting an initial limit value, the initial limit value indicating that the sample has increased in temperature from the ambient to the point where significant amounts of volatile material are driven from the sample.

11. An apparatus for determining the volatile material content of a sample, comprising:
   a. an enclosure;
   b. a weighing platform located within the enclosure for supporting the sample;
   b. means for determining the initial weight of the sample;
   c. means for applying microwave energy to the sample during a variable drying period, said variable drying period including a plurality of portions;
   d. means for monitoring the rate of weight loss of the sample during the variable drying period; and
   e. means for controlling the application of microwave energy to the sample during the variable drying period in response to the monitored weight loss rate to determine the length of the variable drying period with said microwave energy being applied intermittentally during a portion of the variable drying period thereby precisely controlling the drying of the sample;
   f. means for determining the final weight of the sample at the end of the variable drying period; and
   g. means for determining the loss of volatile material from the sample by using the final weight and the initial weight.

12. The apparatus of claim 11 wherein the volatile material comprises water.

13. The apparatus of claim 11 wherein the means for determining the initial weight of the sample includes:
   a. a balance; and
   b. a computer connected to said balance and programmed to obtain the initial weight information the balance.

14. The apparatus of claim 11 wherein the means for controlling includes a computer.

15. The apparatus of claim 11 wherein the means for controlling includes:
   a. means for applying uninterrupted microwave energy to the sample during a first portion of the variable drying period; and
   b. means for applying microwave energy intermittentally to the sample during a second portion of the variable drying period.

16. The apparatus of claim 15 wherein said first portion includes
   a. an initial portion during which the sample's temperature increases from the ambient temperature to a temperature where the volatile material beings to be driven from the sample at a substantially higher rate than during the initial portion, the volatile material being driven from the sample at a substantially slow rate during the initial period; and
   b. a middle portion during which the volatile material is driven from the sample at a rate substantially higher than the substantially slow rate provided during the initial portion.

17. The apparatus of claim 16 wherein the second portion follows the middle portion and during the second portion the volatile material is driven from the sample at a substantially lower rate than during the middle portion.

18. The apparatus of claim 11 wherein the weighing platform is fabricated from a material that is unreactive to microwave energy.

19. The apparatus of claim 11 wherein the means for controlling includes:
   a. means for applying uninterrupted microwave energy to the sample until a first limit value is detected, the first limit value indicating that most of the volatile material has been driven from the sample; and
   b. means for applying microwave energy intermittentally to the sample until a second limit value is detected, the second limit value indicating that further application of microwave energy to the sample could result in damage of the sample.

20. The apparatus of claim 19 wherein the means for applying uninterrupted microwave energy applying includes a means for detecting an initial limit value, the initial limit value indicating that the sample has increased in temperature from the ambient to the point where significant amounts of volatile material are being driven from the sample.

* * * * *